US012778915B2

(12) United States Patent
Della Valle et al.

(10) Patent No.: US 12,778,915 B2
(45) Date of Patent: Nov. 3, 2026

(54) N-PALMITOYL-ETHANOLAMIDE FOR USE IN THE PREVENTION OF COLORECTAL CARCINOMA

(71) Applicants: EPITECH GROUP S.P.A., Milan (IT); Maria Federica Della Valle

(72) Inventors: Francesco Della Valle, Milan (IT); Maria Federica Della Valle, Milan (IT); Chiara Gomiero, Milan (IT); Francesca Borrelli, Milan (IT); Raffaele Capasso, Milan (IT); Angelo Antonio Izzo, Milan (IT); Ester Pagano, Milan (IT); Barbara Romano, Milan (IT)

(73) Assignee: Epitech Group S.P.A., Milan (IT)

(*) Notice: Subject to any disclaimer, the term of this patent is extended or adjusted under 35 U.S.C. 154(b) by 1118 days.

(21) Appl. No.: 17/691,572

(22) Filed: Mar. 10, 2022

(65) Prior Publication Data

US 2022/0296541 A1 Sep. 22, 2022

(30) Foreign Application Priority Data

Mar. 18, 2021 (IT) ........................ 102021000006494

(51) Int. Cl.

| | |
|---|---|
| ***A61K 31/164*** | (2006.01) |
| ***A61K 9/02*** | (2006.01) |
| ***A61K 9/06*** | (2006.01) |
| ***A61K 9/14*** | (2006.01) |
| ***A61K 9/16*** | (2006.01) |
| ***A61K 9/20*** | (2006.01) |
| ***A61K 9/28*** | (2006.01) |
| ***A61K 9/48*** | (2006.01) |
| ***A61P 35/00*** | (2006.01) |

(52) U.S. Cl.

CPC .............. *A61K 31/164* (2013.01); *A61K 9/02* (2013.01); *A61K 9/06* (2013.01); *A61K 9/14* (2013.01); *A61K 9/1623* (2013.01); *A61K 9/2018* (2013.01); *A61K 9/2027* (2013.01); *A61K 9/2054* (2013.01); *A61K 9/284* (2013.01); *A61K 9/2866* (2013.01); *A61K 9/4891* (2013.01); *A61P 35/00* (2018.01)

(58) Field of Classification Search

CPC .......... A61K 31/164; A61K 9/02; A61K 9/06; A61K 9/14; A61K 9/1623; A61K 9/2018; A61K 9/2027; A61K 9/2054; A61K 9/284; A61K 9/2866; A61K 9/4891; A61K 9/0031; A61K 9/4858; A61K 47/14; A61K 47/44; A61P 35/00; A61P 31/00

See application file for complete search history.

(56) References Cited

FOREIGN PATENT DOCUMENTS

WO 2011027373 A1 3/2011

OTHER PUBLICATIONS

Partial English translation of Italian Search Report and Written Opinion for Italian Patent Application No. 102021000006494, mailed Nov. 23, 2021, 15 pages.

Giovanni Sarnelli et al: "Palmitoylethanolamine Modulates Inflammation-Associated Vascular Endothelial Growth Factor (VEGF) Signaling via the Akt/mTOR Pathway in a Selective Peroxisome Proliferator-Activated Receptor Alpha (PPAR-α)-Dependent Manner", PLOS One, vol. 11, No. 5, May 24, 2016, 14 pages.

Pagano E. et al: "Key role of palmitoyelthanolamine in experimental colon carcinogenesis", Aug. 1, 2021, XP055860166, Database accession No. EMB-623864476, 3 pgs.

Cordaro Marika et al: "An Update of Palmitoyethanolamine and Luteolin Effects in Preclinical and Clinical Studies of Neuroinflammatory Events", ANTIOXIDANTS, No. 9, No. 5, Mar. 5, 2020, 28 pages.

Mornishi Tatsuya et al: "Activation and Expression of Peroxisome Proliferator-Activated Receptor Alpha Are Associated with Tumorigenesis in Colorectal Carcinoma", PPAR Research, vol. 2019, Jul. 3, 2019, pp. 1-9.

Couch Daniel G. et al. "Cannabidiol and palmitoyethanolamide are anti-inflammatory in the acutely inflamed human colon", Clinical Science, vol. 131, No. 21, Nov. 1, 2017, pp. 2611-2226.

Pagano Ester et al: "Palmitoyehtanolamide Reduces Colon Cancer Cell Proliferation and Migration, Influences Tumor Cell Cycle and Exerts In Vivo Chemopreventative Effects", CANCERS, vol. 13, No. 8, Apr. 16, 2021, pp. 1-14.

Sarnelli Giovanni et al: "Palmitoyehtanolamide Exerts Antiproliferative Effect and Downregulates VEGF Signaling in Caco-2 Human Colon Carcinoma Cell Like Through a Selective PPAR-[alpha]-Dependent Ihibition of Akt/mTOR Pathway", Physiotherapy Research, vol. 30., No. 6, Mar. 2016, pp. 963-970.

Pileggi et al. "Information about management of chronic drug therapies prescribed at hospital discharge: does it affect patients' knowledge and self-confidence?" BMC Health Services Research (2018) 18:105. 10 pages.

Verhoechx et al., "The Impact of Food Bioactives on Health: in vitro and ex vivo models [Internet]", Chapter 10, Springer Cham, 2015, pp. 103-111.

*Primary Examiner* — Jessica Worsham

(74) *Attorney, Agent, or Firm* — Armstrong Teasdale LLP

(57) ABSTRACT

Described herein is a use of N-palmitoylethanolamide in the context of an antitumor therapy, in particular, a use of Palmitoylethanolamide in the prevention of colorectal carcinoma, adenomatous polyps, and/or pre-neoplastic ACF lesions. Also described herein are palmitoylethanolamide for use in the antineoplastic therapy of colorectal carcinoma, in which the palmitoylethanolamide exerts a selective antiproliferative action on tumor cells and not on healthy cells.

9 Claims, 5 Drawing Sheets

N-PALMITOYL-ETHANOLAMIDE FOR USE IN THE PREVENTION OF COLORECTAL CARCINOMA

CROSS-REFERENCE TO RELATED APPLICATIONS

This application claims priority to Italian Patent Application No. 102021000006494, having a filing date of Mar. 18, 2021, which is hereby incorporated by reference in its entirety.

TECHNICAL FIELD OF THE INVENTION

The present invention relates to the use of N-palmitoylethanolamide in the context of an antitumor therapy.

BACKGROUND ART

Colorectal cancer (CRC) is a very common neoplastic disease and is a leading cause of death with a rapidly increasing incidence rate worldwide. It was estimated that 147,950 individuals received a new diagnosis of CRC in the United States in 2020, with 17,930 new cases (12%) in individuals under the age of 50. In Europe, CRC was second in the ranking of cancer deaths in 2018.

It has been estimated that every year, about 53,000 new diagnoses of colorectal cancer (CRC) are formulated in Italy and this disease is in second place, in order of frequency, in both men and women. Since the mid-2000s, the incidence of CRC has steadily increased due to the increase in risk factors favoring the development thereof.

Many factors trigger the onset mechanisms of this tumor, including lifestyle, unbalanced diet, genetic factors, alterations in the intestinal microbiota, inflammatory bowel diseases (IBD) and other diseases such as Crohn's disease, ulcerative colitis, familial adenomatous polyposis (FAP) and Lynch syndrome.

The incidence of CRC began to decrease coinciding with the introduction of screening and drug-prevention or chemoprevention programs consisting of the use of substances which have been shown to reduce the risk of solid tumors appearing.

Chemo-prevention is that branch of oncology which is aimed at healthy people who may have an increased risk of developing cancer and tries to act in that broad time window during which the molecular alteration processes which cause cancer to occur. For this reason, preventive strategies aim to eliminate or reduce exposure to carcinogens, to identify subjects at risk and to intervene to interrupt the process of carcinogenesis, with a pharmacological and/or dietary action. Chemo-prevention tries to hinder neoplastic transformation by acting on both the activation phase and on proliferation.

The difference with respect to chemotherapy is very great, whereby the two approaches must not be confused: preventive treatment involves the use of substances which do not have harmful effects on healthy cells and therefore on the health of the person subjected to them. Conversely, in chemotherapy treatment, harmful chemicals are used which are directed not only at diseased cells, but also healthy ones. Therefore, chemo-prevention has the purpose of creating and maintaining a constant homeostatic balance to prevent the uncontrolled reproduction of cells.

CRC in humans occurs in the final stretch of the digestive tract and is due to the malignant transformation of polyps following the uncontrolled proliferation of intestinal mucosal cells. Polyps are considered precancerous forms, although they fall under benign pathologies.

In most cases, CRC begins as a benign adenomatous polyp from which a highly dysplastic adenoma develops which, in turn, progresses to invasive cancer due to the accumulation of genetic and epigenetic alterations which determine the progressive loss of genetic stability.

The transformation process of intestinal mucosal cells from normal to cancer in the colorectal area occurs due to mutations in the tumor suppressor genes used to block the progression of the cell cycle, protecting the cell from the accumulation of potentially cancerous mutations. When such a block is missing, the cell progresses towards transformation into a cancer cell in an uncontrolled manner.

To date, the therapy aimed at eradicating CRC is surgery, often preceded by chemo and radiotherapy in order to carry out increasingly conservative interventions and, when possible, to avoid the creation of the so-called ostomy. The most active cancer drugs in the treatment of CRC comprise fluoropyrimidines (intravenous 5-fluorouracil, oral capecitabine), oxaliplatin and irinotecan.

For what has been said above, particularly in relation to the genesis of colorectal carcinoma, it is therefore evident that there is a need to provide a therapy which is capable of preventing the onset of such a tumor form and which, in the case of subjects already suffering from such disease, provide a safe treatment, i.e., one which selectively acts only on cancer cells and does not affect healthy cells.

SUMMARY OF THE INVENTION

The present invention derives from the surprising discovery that palmitoylethanolamide (PEA), preferably if used in ultra-micronized form, is capable of exerting a preventive effect on the formation of colorectal carcinoma (CRC), as well as on the formation of benign adenomatous polyps, and a specific antineoplastic effect on tumor cells.

The present invention relates to Palmitoylethanolamide for use in the prevention of colorectal carcinoma, adenomatous polyps and/or pre-neoplastic ACF lesions.

The invention further relates to Palmitoylethanolamide for use in the antineoplastic therapy of colorectal carcinoma, in which said palmitoylethanolamide exerts a selective antiproliferative action on tumor cells and not on healthy cells.

These and further objects, as outlined in the appended claims, will be described in the following description. The text of the claims must be considered included in the description for the purpose of assessing the sufficiency of the description.

Further features and advantages of the invention will become apparent from the following description of preferred embodiments, given by way of non-limiting example.

DETAILED DESCRIPTION OF THE INVENTION

Figure 1:
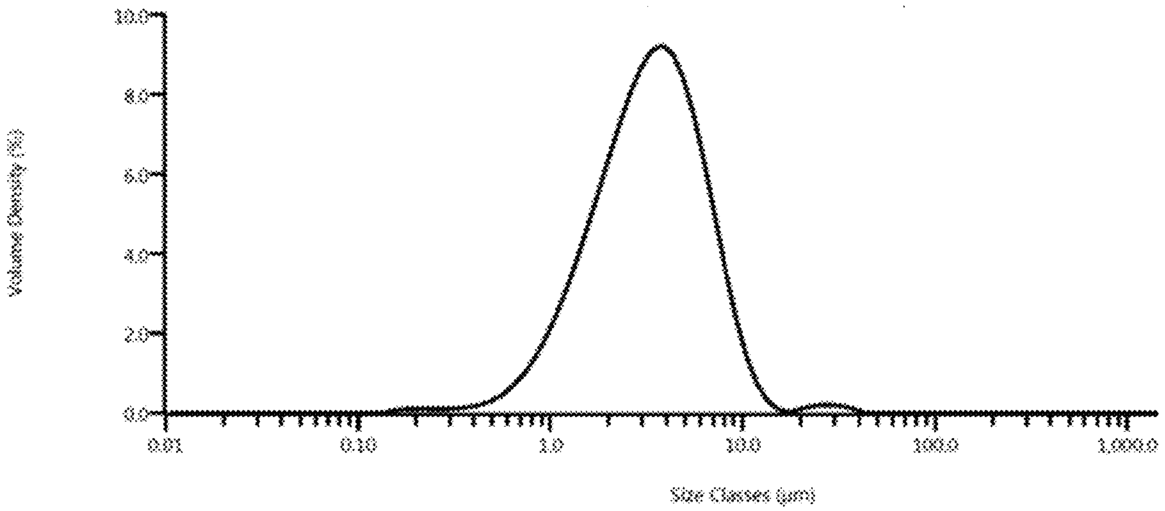
FIG. 1 shows a particle size distribution graph of palmitoylethanolamide in ultra-micronized form.

The present invention relates in a first aspect to palmitoylethanolamide (PEA) for use in the prevention of colorectal carcinoma (CRC).

The term "prevention" means the pharmacological treatment of a healthy patient, preferably a patient at risk of colorectal cancer, in order to hinder the onset of a neoplastic alteration or the neoplastic transformation of a benign formation by acting on both the activation phase and on proliferation.

In particular, by virtue of the present invention, patients at risk of CRC subjected to the search for tumor and inflammatory biomarkers and which test positive for such biomarkers, can be put under chronic PEA therapy, in particular ultra-micronized PEA, to restore the correct intestinal environment in order to counteract and/or slow down the onset of CRC.

In a second aspect, the present invention relates to palmitoylethanolamide (PEA) for use in the antineoplastic therapy of CRC, in which said PEA exerts a selective antiproliferative action on tumor cells and not on healthy cells.

In particular, the invention relates to palmitoylethanolamide (PEA) for use in the antineoplastic therapy of CRC, in which said PEA exerts a selective antiproliferative action on tumor cells by stopping the cell cycle of neoplastic cells in the G2/M phase.

Preferably, the PEA is in ultra-micronized form.

The term "palmitoylethanolamide (or PEA) in ultra-micronized form" means PEA having a particle size distribution, defined as a percentage by volume and measured with the laser light scattering method, represented by a distribution curve having the mode below 6 microns and above 0.5 microns.

In an embodiment, the PEA in ultra-micronized form has a particle size distribution as defined above, measured with a Malvern Mastersizer 3000 instrument with Fraunhofer calculation algorithm, where at least 95% by volume, more preferably at least 99% by volume, of particles has a particle size of less than 6 microns.

In a particularly preferred embodiment, the PEA in ultra-micronized form has a particle size distribution as defined above, measured with a Malvern Mastersizer 3000 instrument with Fraunhofer calculation algorithm, having a mode between 2 and 4 microns and having 100% by volume of particles smaller than 10 microns and at least 60% by volume of particles smaller than 3 microns.

The micronization can be carried out in a fluid jet system (for example, Jetmill® model system) which operates with spiral technology with a compressed air or nitrogen jet capable of exploiting kinetic energy—instead of mechanical energy—to crush the particles. Such apparatuses are conventional and will therefore not be further described, except in relation to the following features:

Internal diameter of the micronization chamber about 300 mm;

Fluid jet pressure 10-12 bar;

Product supply 9-12 kg/h.

For the purposes of the invention, the PEA can be included in pharmaceutical or veterinary formulations and can be formulated in dosage forms for oral, buccal, parenteral, rectal or transdermal administration.

For oral administration, the pharmaceutical compositions can be, for example, in the form of tablets or capsules, hard or soft, prepared in the conventional fashion with pharmaceutically acceptable excipients such as binding agents (e.g., pregelatinized cornstarch, polyvinylpyrrolidone or methylcellulose hydroxypropyl); filling agents (e.g., lactose, microcrystalline cellulose or calcium hydrogen phosphate); lubricants (e.g., magnesium stearate, talc or silica); disintegrants (e.g., potato starch or sodium starch glycolate); or inhibiting agents (e.g. sodium lauryl sulfate). The tablets can be coated with the methods well known in the art. The liquid preparations for oral administration can be, for example, in the form of solutions, syrups or suspensions or they can be freeze-dried or granulated products to be reconstituted, before use, with water or other suitable vehicles. Such liquid preparations can be prepared through conventional methods with pharmaceutically acceptable additives such as suspending agents (e.g., sorbitol syrup, cellulose derivatives, or edible hydrogenated fats); emulsifying agents (e.g., lecithin or acacia); non-aqueous vehicles (e.g., almond oil, oily esters, ethyl alcohol or fractionated vegetable oils); and preservatives (e.g., methyl- or propyl-p-hydroxybenzoates or sorbic acid). The preparation can also conveniently contain flavorings, dyes, and sweetening agents.

The preparations for oral administration can be formulated appropriately to allow the controlled release of the active constituent.

For buccal administration, the compositions can be in the form of tablets or pills formulated in the conventional fashion, adapted to an absorption at the level of the buccal mucosa. Typical buccal formulations are tablets for sublingual administration.

The composition of the invention can be formulated for parenteral administration by injection. The injection formulations can be presented as a single dose, for example in vials, with an added preservative. The compositions can appear in this form as suspensions, solutions, or emulsions in oily or aqueous vehicles and can contain agents of the formulation such as suspension, stabilizing and/or dispersing agents. Alternatively, the active constituent can be in the form of a powder to be reconstituted, before use, with a suitable vehicle, for example with sterile water.

The composition of the invention can also be formulated according to rectal formulations such as suppositories or retention enemas, for example containing the basic components of the common suppositories such as cocoa butter or other glycerides.

In addition to the compositions described above, the composition of the invention can also be formulated as a deposit preparation. Such long-acting formulations can be administered by implantation (e.g., subcutaneously, transcutaneously or intramuscularly) or by intramuscular injection. Thus, for example, the composition can be formulated with appropriate polymeric or hydrophobic materials (for example in the form of an emulsion in a suitable oil) or ion exchange resins or as minimally soluble derivatives.

According to the present invention, the dose of PEA proposed for administration to a human (with a body weight of about 70 kg) ranges from 10 mg to 1500 mg or from 100 mg to 900 mg of PEA per dose unit. The dose unit can be administered, for example, 1 to 4 times a day. The dose will depend on the form in which the PEA is administered, i.e., whether non-micronized PEA, micronized PEA or ultra-micronized PEA is administered. The dose will also depend on the route chosen for administration. It should be considered that it may be necessary to continuously vary the dosage depending on the age and weight of the patient and also on the severity of the clinical condition to be treated. The exact dose and route of administration will ultimately be at the discretion of the attending physician or veterinarian.

For a preventive treatment, the PEA can be administered for prolonged periods or for a chronic preventive treatment, by virtue of the very low toxicity thereof.

The invention further relates to dietary compositions, food supplements and foods for special medical purposes (FSMPs) comprising PEA, preferably ultra-micronized PEA for use in the prevention of the onset of CRC in a healthy subject.

The term "food for special medical purposes" means products authorized according to regulation (EU) 2016/128. Such a term refers to a product to be administered under medical supervision, thus assimilating such an FSMP to a drug.

The formulations according to the invention can be prepared according to conventional methods, such as those described in Remington's Pharmaceutical Sciences Handbook, Mack Pub. Co., N.Y., USA, 17th edition, 1985.

Experimental Part

Micronization Procedure

The PEA was micronized as previously described.

The ultra-micronization was carried out in a fluid jet system (in particular, the Jetmill® model system) which operates with compressed air jet "spiral technology".

Optimal Micronization Conditions:

- internal diameter of the micronization chamber 300 mm;
- fluid jet pressure 8 bar;
- product supply 9-12 kg/h.

Determination of the Particle Size Distribution

The determination of the particle size distribution was carried out on a wet sample, after 1-minute sonication.

A Malvern Mastersizer 3000 instrument operating with the LALLS (Low Angle Laser Light Scattering) technique and a Fraunhofer calculation algorithm was used.

The particle size distribution graph is shown in FIG. 1.

Biological Experimentation

For the in vitro experiments, immortalized human colon cancer (HCT116) and human colorectal adenocarcinoma cell lines (Caco-2) and immortalized healthy human colon epithelial cells (HCEC) were cultured in DMEM growth medium (Sigma Aldrich) supplemented with 10% serum bovine fetal (FBS, Sigma Aldrich) and kept at 37° C. in an incubator with a 5% $CO_2$ atmosphere.

To assess viability, the cells are stained with Trypan blue while cell proliferation, in the presence or absence of ultra-micronized PEA (1-30 μM), was determined using the BrdU proliferation ELISA kit (Roche, Milan, Italy).

The cell cycle analysis of HCT116 cells was performed following the protocol reported in the BD Pharmingen™ BrdU Flow Kit (BD Biosciences, USA). For the study, $1.5\times10^5$ cells was sown on 6-well plates and kept overnight in serum-free medium in the presence or absence of ultra-micronized PEA (30 μM) for 24 h. The cells were detected with the BriCyte flow cytometer (Mindray, Italy) according to the BrdU (bromodeoxyuridine) and 7-AAD (7-aminoactinomycin D) content thereof. The data obtained were analyzed with FlowJo v10 software (tree Star, USA) to understand the distribution of HCT116 in the different cell cycle phases.

The expression of the CDK1 and CYCLIN B1 genes was evaluated by virtue of the quantitative Real-Time PCR method using specific primers.

The in vivo study was conducted on six-week-old (25-30 g) male CD1 mice fed ad libitum and housed in cages with a controlled sleep/wake cycle. Before the start of the experimentation, the animals were subjected to an acclimatization period of 1 week considering all the experimental procedures and protocols, compliant with the principles of the care of laboratory animals approved by the Italian Ministry of Health and respecting the ARRIVE guidelines [Curtis M J et al. Experimental design and analysis and their reporting II: updated and simplified guidance for authors and peer reviewers. Br J Pharmacol, 2018; 175: 987-993].

The animals were chemically treated with AOM (azoxymethane, 40 mg/kg in total) [Neufert C et al. An inducible mouse model of colon carcinogenesis for the analysis of sporadic and inflammation-driven tumor progression. Nat Protoc 2007; 2: 1998-2004] to induce the formation of the CRC. A single dose of AOM was injected intraperitoneally at a concentration of 10 mg/kg at the beginning of the first, second, third and fourth weeks of the experiment [Pagano E et al. Pharmacological inhibition of MAGL attenuates experimental colon carcinogenesis, Pharmacol Res 2017; 119: 227-236].

The animals were randomized into 2 groups of 7 animals each:

- Group 1 was treated per os with 2% carboxymethylcellulose (CMC), vehicle used to suspend the ultra-micronized PEA.
- Group 2 was treated per os with ultra-micronized PEA in 2% CMC at a concentration of 10 mg/kg three times a week for the duration of the experiment, starting the week before the first administration of AOM to appreciate the chemo-preventive effect thereof [Pagano E et al. Pharmacological inhibition of MAGL attenuates experimental colon carcinogenesis, Pharmacol Res 2017; 119: 227-236].

The animals were euthanized 12 weeks after the first AOM injection and the colorectal area was collected.

Based on laboratory experience, the timing and dose of AOM used ensure the appearance of a significant number of ACF, polyps and tumors [Izzo A A et al. Increased endocannabinoid levels reduce the development of precancerous lesions in the mouse colon. J Mol Med (Berl) 2008; 86: 89-98].

The detection and quantification of ACF, polyps and colorectal tumors was performed following the protocol of Pagano E et al. Pharmacological inhibition of MAGL attenuates experimental colon carcinogenesis, Pharmacol Res 2017; 119: 227-236.

Results

Proliferation of HCT116 and Caco-2 Cells In Vitro

Figure 2A:
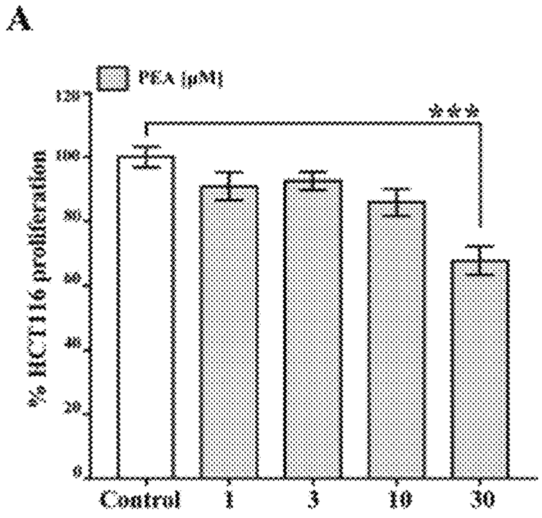
FIGS. 2A, 2B and 2C depict graphs of the cell proliferation rate of HCT116 (A), Caco-2 (B) cells and healthy human colon epithelial cells HCEC (C) in the presence or in the absence of ultra-micronized PEA for 24 h, in which the results are expressed as a cell proliferation percentage as averages±SEM; *P<0.05 and ***P0<0.001 with respect to the control group and evaluated with Student's t test (ns=not significant)
Figure 2B:
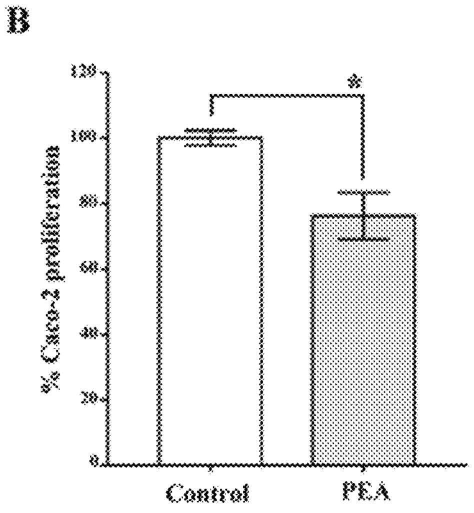
Figure 2C:
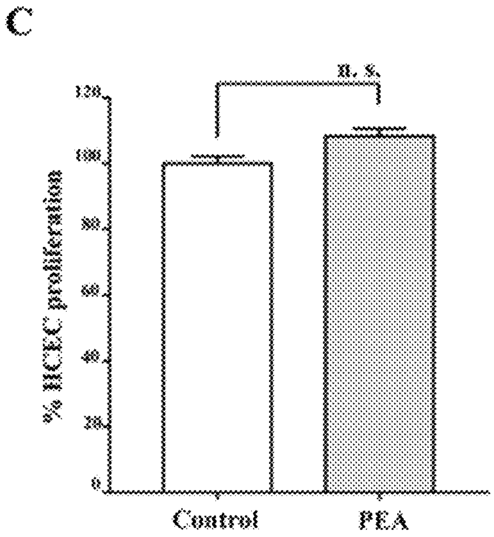

Ultra-micronized PEA significantly reduces the proliferation of HCT116 and Caco-2 cells in vitro; specifically, ultra-micronized PEA, used at increasing doses (1-30 μM), reduces the proliferation rate of HCT116 cells during the 24 hours of exposure (FIG. 2A). Furthermore, 30 μM ultra-micronized PEA is capable of significantly reducing the proliferation of non-metastatic Caco-2 cells (FIG. 2B). Surprisingly, the anti-proliferative effects of the ultra-micronized PEA did not affect the proliferation rate of the healthy epithelial cell line HCEC (FIG. 2C), effectively showing a selective effect on tumor cells. This datum is very important because it allows a considerable reduction of side effects.

Cell Cycle Arrest in the G2/M Phase of HCT116 Cells In Vitro

Figure 3A:
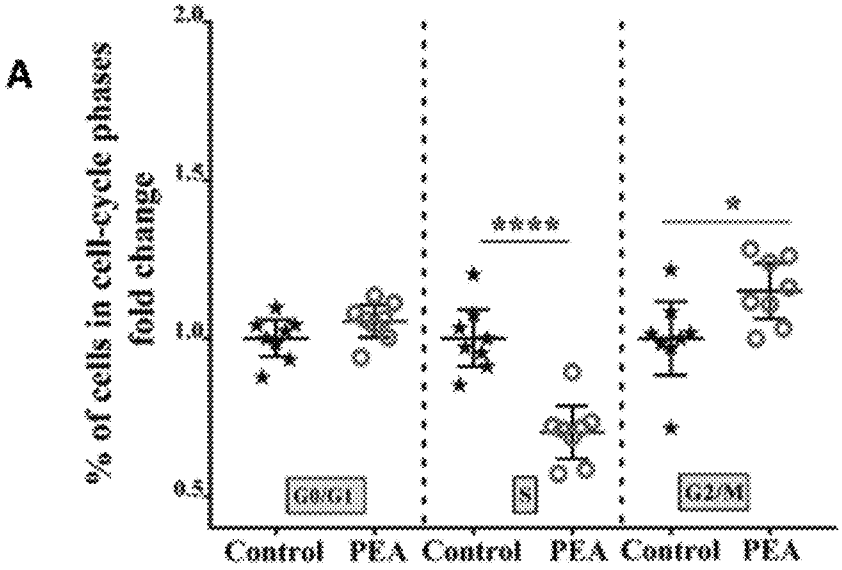
FIGS. 3A, 3B and 3C depict graphs of the induction of cell cycle arrest by ultra-micronized PEA: (A) Cell cycle analysis by flow cytometry of HCT116 cells in the presence or absence of ultra-micronized PEA (30 μM for 24 h), *P<0.05 and ****P<0.0001 vs. control evaluated with Student's t-test; Gene expression of cyclin B1 (B) and cyclic-dependent kinase 1 (CDK1) (C) in HCT116 cells, in the presence or absence of ultra-micronized PEA (30 μM for 24 h); the expression of the genes was measured with Real-Time PCR and the results are expressed as averages±SEM; *P<0.05 and ***P0<0.001 with respect to the control group and evaluated with Student's t test.
Figure 3B:
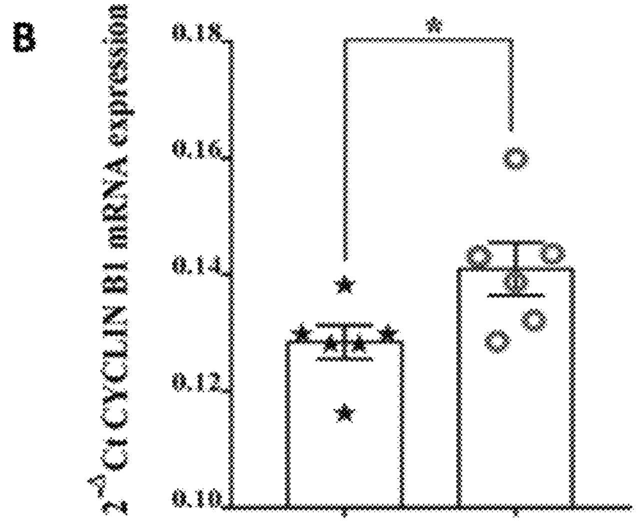
Figure 3C:
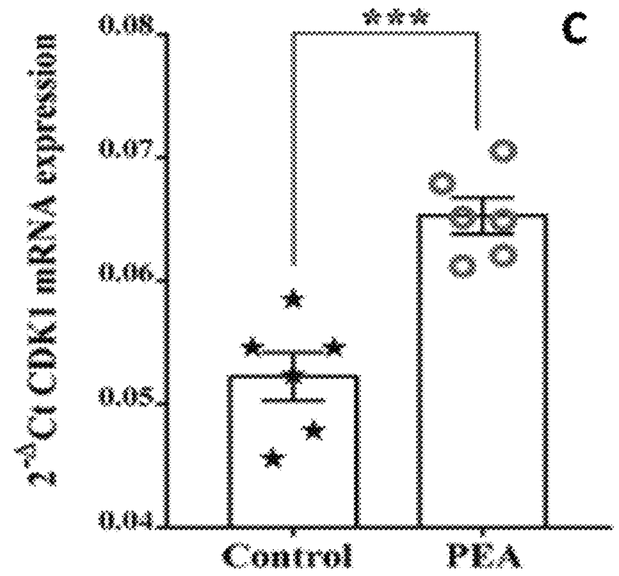

Flow cytometry revealed that the treatment of the HCT116 cells with ultra-micronized PEA (30 μM for 24 h) is capable of blocking neoplastic cells in the G2/M phase with a concomitant significant reduction in the percentage of cells in the S phase (FIG. 3A). Since it is known that the G2/M transition is regulated by the cyclin B1/CDK1 complex [Malumbres M and Barbacid M, 2005], we explored the behavior of such a complex in the presence of ultra-micronized PEA: we found that the treatment of cells with ultra-micronized PEA induces increased expression of the cyclin B1/CDK1 complex (FIG. 3B-C). These data demonstrate the ability of ultra-micronized PEA to actively participate not only in the arrest of neoplastic cells in the G2/M phase but also in the activation of the cyclin B1/CDK1 complex necessary for the arrest of the cell cycle in the aforesaid phase.

Prevention of Tumor Development in the Animal Model of CRC

Figure 4A:
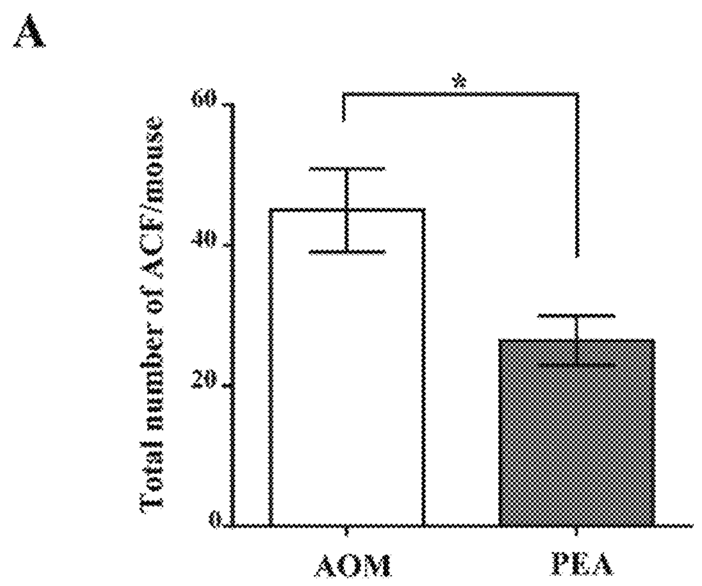
FIGS. 4A, 4B and 4C depict graphs of the effect of ultra-micronized PEA treatment in the AOM mouse model of colon cancer: (A) total number of ACFs, (B) polyps and (C) tumors derived from the administration of AOM (10 mg/kg at the beginning of the first, second, third and fourth week of experimentation corresponding to 40 mg/kg total intraperitoneally) in mice treated or not treated with ultra-micronized PEA 10 mg/kg per os three times a week for the duration of the trial (13 weeks) starting the week before the first administration of AOM to appreciate the chemo-preventive effect thereof; the results are expressed as averages±SEM; *p<0.05 and **p<0.01 with respect to the group treated with AOM alone using Student's t-test.
Figure 4B:
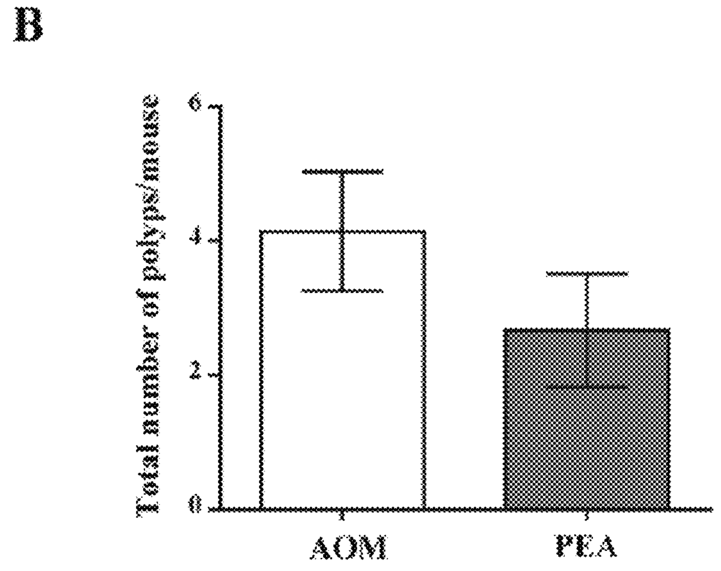
Figure 4C:
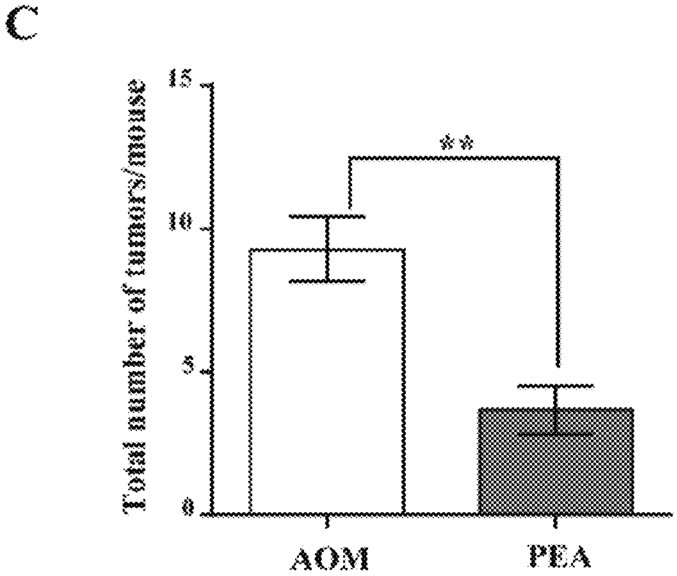

Administration of the carcinogen AOM (azoxymethane) induces the formation of several foci of aberrant crypts, known as ACF (FIG. 4A), polyps (FIG. 4B) and tumors (FIG. 4C). The treatment of animals with ultra-micronized PEA 10 mg/kg, administered per os three times a week for the duration of the experiment (13 weeks), starting the week before the first AOM administration, significantly reduces the number of pre-neoplastic ACF lesions (FIG. 4A) and the total number of tumors (FIG. 4C) induced by the carcinogen AOM. The ultra-micronized PEA showed a strong tendency to also reduce the number of polyps (FIG. 4B).

In light of these results, the preventive administration of ultra-micronized PEA appears to be effective in reducing the development of CRC by virtue of the slowing of the transformation of intestinal mucosal cells into tumor cells (chemo-preventive effect). This datum demonstrates how the preventive intake of ultra-micronized PEA, in addition to being completely safe, significantly attenuates the aggressiveness of CRC, effectively improving life expectancy.

Furthermore, the slow transformation of mucosal cells allows, at the time of diagnosis, to treat a small CRC and, most likely, in the early phases of not yet aggressive staging.

The data obtained show, for the first time, how chemo-preventive treatment with PEA and in particular with ultra-micronized PEA, is capable of reducing the development of CRC.

Therefore, the invention further relates to a method of preventing colorectal carcinoma, adenomatous polyps and/or pre-neoplastic ACF lesions in healthy subjects coomprising administering an effective amount of palmitoylethanolamide, either non-micronized, micronized, ultra-micronized or a in a mixture thereof.

Moreover, the invention relates to a method of treating a colorectal carcinoma in a patient in need thereof by administering an effective amount of palmitoylethanolamide, wherein said palmitoylethanolamide exerts a selective anti-proliferative action on tumor cells and not on healthy cells and wherein said palmitoylethanolamide is either non-micronized, micronized, ultra-micronized or a in a mixture thereof.

The invention will now be further described by means of the following formulation examples.

Formulation Examples

PEA-UM=Ultra-micronized palmitoylethanolamide

Example 1

Each tablet contains:

| | |
|---|---|
| PEA-UM | 300.00 mg |
| Macrocrystalline cellulose | 78.47 mg |
| Sodium croscarmellose | 45.00 mg |
| Polyvinylpyrrolidone | 10.00 mg |
| Magnesium stearate | 4.0 mg |
| Polysorbate 80 | 2.00 mg |

Example 2

Each tablet contains:

| | |
|---|---|
| PEA-UM | 600.00 mg |
| Macrocrystalline cellulose | 156.94 mg |
| Sodium croscarmellose | 90.00 mg |
| Polyvinylpyrrolidone | 20.00 mg |
| Magnesium stearate | 8.00 mg |
| Polysorbate 80 | 4.00 mg |

Example 3

A 5 g dose of orodisintegrating microgranules contains:

| | |
|---|---|
| PEA-UM | 500.00 mg |
| Non-cariogenic sugar | 200.00 mg |
| acceptable excipients as needed to 5.00 g | |

Example 4

A hard gelatin capsule made gastro-resistant with an adequate coating contains:

| | |
|---|---|
| PEA-UM | 400 mg |
| Soy lecithin | 100 mg |
| Lactose | 80 mg |

Example 5

A tablet coated with a gastro-resistant layer contains:

| | |
|---|---|
| PEA-UM | 500 mg |
| Micronized PEA | 250 mg |

-continued

| | |
|---|---|
| Polyvinylpyrrolidone | 30 mg |
| Sodium croscarmellose | 80 mg |
| Magnesium stearate | 7 mg |

Example 6

A suppository contains:

| | |
|---|---|
| PEA-UM | 300 mg |
| Non-micronized PEA | 500 mg |
| Lipophilic mass for suppositories as needed to 3 g | |

Example 7

A 2.5 ml dose of oily gel contains

| | |
|---|---|
| PEA-UM | 600.00 mg |
| Glyceryl monostearate | 40.00 mg |
| Vegetable oil as needed to 2.50 ml. | |

What is claimed:

1. A method of preventing colorectal carcinoma, adenomatous polyps, and/or pre-neoplastic ACF lesions in healthy subjects, the method comprising administering an effective amount of palmitoylethanolamide (PEA), either non-micronized, micronized, ultra-micronized, or a mixture thereof, wherein said palmitoylethanolamide is acting on both the activation and proliferation phase and wherein palmitoylethanolamide is contained in a pharmaceutical or veterinary formulation or in dietary compositions, food supplements, or foods for special medical purposes (FSMPs).

2. The method according to claim 1, wherein palmitoylethanolamide is in ultra-micronized form having a particle size distribution, defined as percentage by volume and measured by a laser light scattering method, represented by a distribution curve having the mode below 6 microns and above 0.5 microns.

3. The method according to claim 2, having a particle size distribution, defined as percentage by volume and measured by the laser light scattering method, measured with a Malvern Mastersizer 3000 instrument with Fraunhofer calculation algorithm, wherein at least 95% by volume of particles has a particle size less than 6 microns.

4. The method according to claim 2, wherein the palmitoylethanolamide has a particle size distribution, defined as percentage by volume and measured by the laser light scattering method, measured with a Malvern Mastersizer 3000 instrument with Fraunhofer calculation algorithm, having a mode between 2 and 4 microns and having 100% by volume of particles smaller than 10 microns and at least 60% by volume of particles smaller than 3 microns.

5. The method according to claim 1, wherein palmitoylethanolamide is administered in doses of 10 mg to 1500 mg or 100 mg to 900 mg of PEA per dose unit, 1 to 4 times per day.

6. The method according to claim 1, wherein palmitoylethanolamide is formulated in dosage forms for oral, buccal, parenteral, rectal, or transdermal administration.

7. The method according to claim 1, wherein said palmitoylethanolamide is used in a chronic administration.

8. The method according to claim 3, wherein at least 99% by volume of particles has a particle size less than 6 microns.

9. A method of preventing colorectal carcinoma, adenomatous polyps, and/or pre-neoplastic ACF lesions in healthy subjects, the method comprising administering an effective amount of ultra-micronized palmitoylethanolamide (PEA), wherein said palmitoylethanolamide is acting on both the activation and proliferation phase and wherein palmitoylethanolamide is contained in a pharmaceutical or veterinary formulation or in dietary compositions, food supplements, or foods for special medical purposes (FSMPs), and wherein the ultra-micronized palmitoylethanolamide is administered in a dose of 10 mg/kg, three times per week.

* * * * *